US005627121A

United States Patent [19]
Lin et al.

[11] Patent Number: 5,627,121
[45] Date of Patent: May 6, 1997

[54] PROCESS FOR PREPARING ALKOXYLATION CATALYSTS AND ALKOXYLATION PROCESS

[75] Inventors: John Lin, Cedar Park; Upali Weerasooriya; Bruce E. Leach, both of Austin; Steve V. Orsak, Cedar Park, all of Tex.

[73] Assignee: Condea Vista Company, Houston, Tex.

[21] Appl. No.: 490,990

[22] Filed: Jun. 15, 1995

[51] Int. Cl.$^6$ .................................................. B01J 31/00
[52] U.S. Cl. ........................ 502/170; 502/172; 502/340
[58] Field of Search ................................ 502/170, 172, 502/340

[56] References Cited

U.S. PATENT DOCUMENTS

| | | | |
|---|---|---|---|
| 4,754,075 | 6/1988 | Knopf et al. | 568/618 |
| 4,775,653 | 10/1988 | Leach et al. | 502/170 |
| 4,820,673 | 4/1989 | Knopf et al. | 502/167 |
| 4,835,321 | 5/1989 | Leach et al. | 568/618 |
| 5,104,987 | 4/1992 | King | 544/401 |
| 5,183,930 | 2/1993 | Venter et al. | 560/217 |
| 5,191,104 | 3/1993 | King | 558/260 |
| 5,220,046 | 6/1993 | Leach et al. | 554/149 |
| 5,386,045 | 1/1995 | Weerasooriya et al. | 568/621 |

*Primary Examiner*—Melvyn I. Marquis
*Assistant Examiner*—Randy Gulakowski
*Attorney, Agent, or Firm*—Browning Bushman

[57] ABSTRACT

A process for preparing an alkoxylation catalyst suitable for alkoxylating compounds such as active hydrogen-containing compounds wherein an alkoxylated alcohol mixture, a calcium-containing compound that is at least partially dispersible in the alkoxylated alcohol mixture, and a carboxylic acid are mixed together to produce a calcium-containing composition having titratable alkalinity, the composition being obtained under conditions to prevent loss of water, the composition being at least partially neutralized with an inorganic acid under conditions to prevent loss of water to produce a partially neutralized calcium-containing catalyst.

16 Claims, No Drawings

PROCESS FOR PREPARING ALKOXYLATION CATALYSTS AND ALKOXYLATION PROCESS

BACKGROUND OF THE INVENTION

The present invention relates to the preparation of an alkoxylation catalyst and to a process of alkoxylation using the thus prepared catalyst.

DESCRIPTION OF THE PRIOR ART

Alkoxylated esters and compounds containing an active hydrogen atom, e.g., alcohols, find utility in a wide variety of products, such as surfactants. Generally, an alkoxylation reaction involving a compound having an active hydrogen is conducted by the condensation of an alkylene oxide using a suitable catalyst. Because of the very nature of the reaction, a mixture of products species is obtained having a rather wide range of molecular weights.

It is now generally recognized that certain ranges of alkoxylated homologs have more desirable properties in certain applications, particularly in the surfactant field. For example, as disclosed in U.S. Pat. Nos. 4,210,764; 4,223,164; 4,254,287; 4,302,613; and 4,306,093, alkoxylated alcohols having a more narrowed or peaked homolog distribution of the alkoxylated species exhibit lower pour points and better detergency than do counterpart products having broader homolog distributions.

U.S. Pat. Nos. 4,835,321; 5,220,046; and 5,386,045, all of which are incorporated herein by reference, disclose the use of calcium-based catalysts in the manufacture of peaked alkoxylated alcohols and carboxylated compounds, respectively. The catalysts employed in the processes of the aforementioned patents utilize, in addition to calcium, an aluminum compound. U.S. Pat. Nos. 4,754,075 and 4,820,673 disclose the manufacture of alkoxylated compounds containing an active hydrogen atoms using calcium-based catalysts that do not contain aluminum. U.S. Pat. Nos. 5,191,104 and 5,104,487, both of which are incorporated herein by reference, disclose the alkoxylation of carboxylated compounds or active hydrogen-containing compounds using mixed metal oxide catalysts or a modified bimetallic or polymetallic catalyst.

SUMMARY OF THE INVENTION

It is therefore an object of the present invention to provide an improved process for alkoxylating the reactants selected from the class consisting of compounds having active hydrogen atoms, esters, and mixtures thereof.

It is a further object of the present invention to provide a process for producing a catalyst useful in the production of alkoxylated compounds having a peaked distribution of the alkoxylated species.

The above and other objects of the present invention will become apparent from the description given herein and the appended claims.

In one aspect, the present invention provides a process for preparing an alkoxylation catalyst comprising admixing an alkoxylated alcohol mixture, a calcium-containing compound that is at least partially dispersible in said alkoxylated alcohol mixture, and a carboxylic acid, preferably branched chain, having from about 4 to about 15 carbon atoms, the mole ratio of calcium to the carboxylic acid being from about 15:1 to 1:1, to produce a calcium-containing composition that has titratable alkalinity. The calcium-containing composition is obtained under conditions that prevent loss of water. An inorganic acid is then added to the calcium-containing composition to neutralize at least 25% of the titratable alkalinity, again under conditions to prevent loss of water. This results in a partially neutralized calcium-containing catalyst suitable for alkoxylation of active hydrogen-containing compounds and esters.

In another aspect of the present invention, the alkoxylation catalyst is formed as described above, following which a reactant selected from the group consisting of active hydrogen-containing compounds, esters, and mixtures thereof are reacted with an alkylene oxide in the presence of the alkoxylation catalyst under alkoxylation conditions to produce an alkoxylated derivative of the reactant.

DESCRIPTION OF THE PREFERRED EMBODIMENTS

According to the method of the present invention for preparing the alkoxylation catalyst, there is no necessity for water removal as disclosed, for example, in U.S. Pat. No. 4,754,075, nor is there any need to incorporate an aluminum trialkoxide such as disclosed in U.S. Pat. No. 4,775,653 in order to obtain a catalyst that is highly active and that produces an alkoxylation product that has a reduced level of haze, a problem commonly associated with using the catalyst disclosed in U.S. Pat. No. 4,775,653.

In preparing the alkoxylation catalyst according to the process of the present invention, an alkoxylated alcohol mixture and a calcium-containing compound that is at least partially dispersible in the alkoxylated alcohol mixture are admixed together with a carboxylic acid. The alkoxylated alcohols useful in forming the catalyst are those having the general formula:

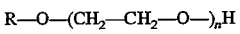

$$R-O-(CH_2-CH_2-O-)_nH$$

wherein R is a hydrocarbon radical (residue of an organic compound) containing from about 1 to about 30 carbon atoms and n is an average of from about 2 to about 20. Particularly useful are alkoxylated alcohols wherein R is from about 8 to about 14, most preferably from about 10 to about 12. In preferred alkoxylated alcohols, n is from about 1 to about 12, most preferably from about 1 to about 4. Thus, ethoxylates of fatty alcohols such as decanol and dodecanol wherein there are from about 1 to about 12, and most preferably from about 1 to about 4, moles of ethylene oxide are especially preferred. The R is generally an organic residue of an aliphatic alcohol that may be of branched or straight chain structure, although, particularly for surfactant use, it is preferred that greater than 50%, more preferably greater than 70% of such alcohol molecules are aliphatic, i.e., preferably having a linear (straight chain) carbon structure.

Specific examples of primary, straight chain monohydric aliphatic alcohols from which the R group can be derived include ethanol, hexanol, octanol, decanol, dodecanol, tetradecanol, pentadecanol, octadecanol, etc. Examples of branched chain or secondary alcohols from which the R group can be derived include isopropanol, isoheptanol, 3-heptanol, isodecanol, 2-methyl-1-nonanol, 2-methyl-1-undecanol, etc.

The alkoxylated alcohol mixture used in the catalyst-forming process of the present invention can be prepared by methods well known in the art for preparing alkylene oxide adducts of alcohol. Alternately, the alkylene oxide adducts can be prepared according to the process of the present invention. The alkoxylated alcohol mixture used in preparing the catalyst of present invention typically contains free alcohol, the amount and type of which will vary depending upon the source of the alkoxylated alcohol. Generally speaking, the alkoxylated alcohol mixture will contain from about 1% to about 60% by weight free alcohol.

The calcium-containing compound used in the process of the present invention is one that is at least partially dispersible in the alkoxylated alcohol. As used herein, the term "dispersible" refers to a calcium compound that solubilizes or otherwise interacts with the alkoxylated alcohol mixture in such a manner that it becomes a new species of calcium compound. It is to be understood, however, that inasmuch as the mechanism is not completely understood, the term "dispersible" or "soluble" is not intended to be limited to the formation of a truly dissolved calcium species, as would be commonly understood in the case of ordinary solubilization. While compounds such as calcium hydride, calcium acetate, calcium oxalate, etc. may be used, it is preferred that the calcium-containing compound be calcium oxide, calcium hydroxide, or a mixture thereof.

It has been found that unless the catalyst preparation utilizes a carboxylic acid, particularly a branched chain carboxylic acid, having from about 4 to about 15 carbon atoms, a suitable catalyst is not prepared. Suitable carboxylic acids are those that have greater miscibility in hydrocarbon solvents than in water. Such acids, which may generally be considered fatty acids, have a carbon chain length versus acid functionality that provides the greater miscibility or solubility in hydrocarbons. Non-limiting examples of such suitable acids include 2-methyl hexanoic acid, heptanoic acid, 3-methyl octanoic acid, 4-ethyl nonanoic acid, 2-ethyl hexanoic acid, etc. While it is preferred that the carboxylic acids be saturated, they may optionally contain other functional groups such as hydroxyl groups, amine groups, etc., that do not interfere with the reaction.

The inorganic acids that are useful in the process of the present invention include the acids themselves as well as "acid salts." Thus, non-limiting examples of inorganic acids include sulfuric acid, hydrochloric acid, hydrofluoric acid, phosphoric acid, polyphosphoric acid, ammonium bifluoride, ammonium sulfate, etc. Particularly preferred are the oxy acids such as sulfuric acid.

When preparing the alkoxylation catalyst of the present invention, the relative amounts of the various components can vary widely. In general, the combined concentration of the calcium compound, the inorganic acid, and the carboxylic acid in the catalyst reaction mixture will be an amount of from about 1% to about 50% by weight, the alkoxylated alcohol mixture (including free alcohol) being present in an amount of from about 50% to about 99% by weight. In general, the mole ratio of calcium, as calcium, to the carboxylic acid will be from about 15:1 to about 1:1. The amount of inorganic acid will vary, depending upon the amount of calcium-containing compound employed, but generally will be in an amount of from about 2% to about 10% by weight of the total concentration of alkoxylated alcohol mixture, calcium-containing compound, carboxylic acid, and inorganic acid.

Surprisingly, it has been found that if in forming the catalyst according to the process of the present invention, the alkoxylated alcohol mixture, the calcium-containing compound, the carboxylic acid, and the neutralizing acid are reacted or combined under conditions that prevent any loss of water that is either initially present or formed during the reaction, a highly active catalyst is formed. It is postulated that by keeping the water in the system during the reaction to form the catalyst, there is enhanced solubilization of the active calcium catalyst species, leading to the production of a more active catalyst. Preventing loss of water is typically accomplished by conducting the reaction at a low enough temperature, e.g., room temperature, to prevent loss of water. Alternately, if the reaction is conducted at elevated temperatures, super-atmospheric pressure can be used to prevent loss of water. Preferably, the reaction is conducted at elevated temperatures under total reflux to prevent loss of water.

In a preferred method of forming the catalyst of the present invention, the calcium-containing compound, e.g., calcium hydroxide, and the alkoxylated alcohol mixture are charged into a suitable stirred vessel equipped with a reflux condenser, following which the carboxylic acid is added. Generally, the three components are mixed at room temperature, although higher temperatures can be used. This reaction mixture is then heated generally to a temperature of from about 30° to 45° C. for a period sufficient to solubilize the calcium-containing compound. Generally speaking, the reaction mixture is reacted for a period of from about 0.5 to about 2 hours. Following solubilization of the calcium compound, a mineral acid—e.g., sulfuric acid—is introduced into the reaction mixture in an amount sufficient to neutralize at least 25% of the titratable alkalinity present in the reaction mixture. The reaction mixture can optionally be sparged with an inert gas such as nitrogen. The partially neutralized reaction mixture is then heated to a temperature of from about 90° C. to about 130° C. under reflux conditions for a period of from about 1 to about 5 hours. The reaction mixture is then raised to a temperature of about 125° to 140° C. and held at this temperature under reflux conditions for a period of from about 10 to 18 hours. Finally, the reaction mixture is heated to a temperature of about 140° to 155° C. for 0.5 to 2 hours. Following this heating step, the reaction mixture is allowed to cool to between 70°–90° C. It is to be noted that at all times when heating is employed in the catalyst preparation procedure, reflux conditions are employed so as to avoid the loss of any water from the reaction mixture.

The catalyst prepared according to the process of the present invention can be used to alkoxylate compounds having active hydrogen atoms, esters, and mixtures thereof.

Suitable active hydrogen-containing compound starting materials (reactants) that can be employed in the alkoxylation process of the present invention include any permissible substituted or unsubstituted active hydrogen-containing organic compound(s). Non-limiting illustrative examples of active hydrogen-containing compounds useful in this invention include, for example, substituted and unsubstituted alcohols, phenols, carboxylic acids, amines, and the like. Preferred active hydrogen-containing compounds include alcohols and phenols, as, for example, substituted and unsubstituted alcohols (mono-, di-, and polyhydric alcohols), phenols, carboxylic acids (mono-, di-, and polyacids), and amines (primary and secondary). Other suitable active hydrogen-containing compounds include substituted and unsubstituted thiophenols, mercaptans, amides, and the like. Such organic compounds frequently contain 1 to about 150 carbons and can contain aliphatic and/or aromatic structures. Most often, the organic compounds are selected from the groups of mono-, di-, and trihydric alcohols having from 1 to about 30 carbon atoms.

Suitable alcohols include primary and secondary monohydric alcohols that are straight or branched chain, such as methanol, ethanol, propanol, pentanol, hexanol, heptanol, octanol, decanol, tridecanol, tetradecanol, isopropyl alcohol, 2-ethylhexanol, 3-pentanol, and isodecanol. Particularly suitable alcohols are linear and branched primary alcohols (including mixtures) such as produced by the "Oxo" reaction of $C_3$ to $C_{20}$ olefins. The alcohols may also be cycloaliphatic, such as cyclopentanol, cyclohexanol, cycloheptanol, etc., as well as aromatic substituted aliphatic alcohols such as benzyl alcohol, phenylethyl alcohol and phenylpropol alcohol.

Phenols that can be used as reactants include alkyl phenols of up to 30 carbons such as p-methylphenol, p-ethylphenol, p-butylphenol, etc.

Alcohols (polyols) having two or more hydroxyl groups, e.g., about 2 to 6 hydroxyl groups, and having 2 to 30 carbon atoms include glycols such as ethylene glycol, propylene glycol, butylene glycol, etc. Other polyols include glycerine, 1,3-propanediol, sorbitol, etc.

Carboxylic acids include formic acid, acetic acid, proprionic acid, valeric acid, lauric acid, stearic acid, oleic acid, linoleic acid, etc. Other suitable carboxylic acids include benzoic acid, phenylacetic acid, toluic acid, phthalic acid, etc.

Amines include methylamine, dimethylamine, ethylamine, diethylamine, n-butylamine, n-dodecylamine, n-dodecylamine, diethanolamine, hexamethylenediamine, etc.

Especially preferred active hydrogen-containing compounds include any permissible active hydrogen-containing organic compound such as those embraced by the formula:

$$R_1(OH)_x$$

wherein $R_1$ is the residue of an organic compound as defined above with respect to R and x is a value that satisfies the valencies of R, x preferably being a value of from about 1 to about 10, more preferably a value of from about 1 to about 4.

Esters that can be alkoxylated via transesterification according to the process of the present invention include monoesters having the formula:

$$R'-\overset{O}{\underset{\|}{C}}-O-R'',$$

alkylene glycol diesters having the formula:

$$R'-\overset{O}{\underset{\|}{C}}-O-(CH_2)_n-O-\overset{O}{\underset{\|}{C}}-R'',$$

and triesters having the formula:

$$\begin{array}{l}R'-\overset{O}{\underset{\|}{C}}-O-CH_2\\R'-\overset{O}{\underset{\|}{C}}-O-CH\\R'-\overset{O}{\underset{\|}{C}}-O-CH_2\end{array}$$

wherein R' and R", which can be the same or different, are each organic radicals containing from about 1 to about 30 carbon atoms; i.e., they can have generally the same connotation as given above for R, and n is from 2 to 12. Such esters and alkoxylated derivatives thereof are disclosed in U.S. Pat. No. 5,386,045, incorporated herein by reference.

In alkoxylating the active hydrogen-containing compounds and esters, an alkylene oxide containing from about 2 to about 4 carbon atoms is employed. Non-limiting examples of such alkylene oxides include ethylene oxide, propylene oxide, etc.

In carrying out the alkoxylation reaction of the present invention, a reactant—e.g., alcohol, ester, or the like—is reacted with an alkylene oxide(s) in the presence of an alkoxylation catalyst prepared as per the process of the present invention. In general, the amount of catalyst employed will be from about 0.1 to about 5% by weight based upon the total reaction mixture. For example, if the weight of the reaction mixture, including all alkylene oxide, is 300 g, typically from about 0.3 g to about 15 g of the alkoxylation catalyst will be employed in the reaction.

The alkoxylation process of the present invention can be conducted over a wide range of temperatures and pressure conditions. For example, the reaction can be conducted at temperatures ranging from about 80° C. or lower to about 200° C. or higher. Pressures can range from subambient up to about 100 psi, pressures of from about 10 to about 60 psi being preferred.

Typically, the alkoxylation reaction of the present invention can be conducted by charging a suitable reaction vessel with the reactant, e.g., alcohol, ester, etc., in the desired amount. Typically, the reactant is heated to the desired elevated temperature under nitrogen or some other suitable inert gas, following which the reactor is placed under vacuum to produce a nitrogen sparge in the reactor to remove water, if present. The alkoxylation catalyst produced as per the present invention is then injected into the reaction mixture and the temperature raised to the desired reaction temperature, the reaction mixture preferably being maintained under a nitrogen blanket. When the desired reaction temperature is reached, the reactor is evacuated and the chosen alkylene oxide, e.g., ethylene oxide, is introduced at the appropriate pressure. As the alkylene oxide reacts, additional amounts are added, the temperature being maintained substantially constant throughout the reaction.

It is important to understand that once the catalyst of the present invention has been formed, water remaining therein can be removed prior to initiation of the alkoxylation reaction. Indeed, depending upon the particular reactants, it may be desirable to dry the alkoxylation catalyst prior to its introduction into the alkoxylation process. This can be accomplished by distillation, usually with a nitrogen sparge. This drying of the formed catalyst is to be distinguished from the production of the catalyst in which water initially present and/or introduced during the reaction to form the catalyst is maintained in the catalyst reaction mixture.

To further illustrate the invention, the following non-limiting examples are presented. In preparing various alkoxylation catalysts, the following procedures were used.

CONTROL A (PROCEDURE OF U.S. PAT. NO. 4,835,321)

In this procedure, 19.53 g of calcium hydroxide and 212.3 g of ALFONIC 10-12-40[1] alcohol ethoxylate mixture was charged to a flask. With efficient stirring at room temperature, 4.46 g 2-ethylhexanoic acid was added in rapid drops over a period of about 3 minutes. The reaction mixture was then heated to 30° C. over a period 0.5 hours with stirring and with the vent to the flask open. This temperature was held constant for 1 hour, after which 4.93 g of concentrated sulfuric acid was introduced from a buret dropwise into the reaction mixture at a rate of 1 drop per 3 seconds. At 15 minutes after completion of the addition, another 4.93 g of concentrated sulfuric acid was introduced in the same manner. Bubbling of nitrogen at a rate of about 200 ml/min. was then commenced. The reaction mixture was heated to 110° C. over a period of 1.5 hours. At 110° C., a vacuum of 22 inches of mercury was carefully applied by slowly closing the vent to the flask using house vacuum. The nitrogen needle valve was readjusted to maintain the approximate 200 ml/min. flow with the established vacuum. When the vacuum and nitrogen bubbling rate were attained, the reaction temperature was raised to 126° C. over a period of 0.5 hours. The reaction was held at 126° C. for 4 hours, after which the vacuum was temporarily interrupted to empty the vacuum trap. Generally, 10 to 12 ml of distillate was collected. With the vacuum reestablished, the temperature was then raised to 138° C. over a period of 0.5 hours. Heating at 138° C. was maintained for 12 to 16 hours. At the end of this holding period, the vacuum and heating were terminated to allow the reaction to cool at 80° C. under nitrogen bubbling. Generally, 5 to 15 ml more distillate was recovered from the trap. A sample of the calcium hydroxide dispersion was collected for water analysis. A 31.61 g aliquot of aluminum trialkoxide, which contains about 6 weight percent aluminum, was quickly introduced into the flask. The pressure was again brought down to 22 inches of mercury with a nitrogen bubble rate of 200 ml/min. Over the next 45 minutes, the temperature was raised to 149° C. This final temperature was maintained for 1 hour, after which the vacuum and heating were discontinued and the reaction mixture allowed to cool to ambient temperature with continued nitrogen bubbling and stirring. About 5 to 10 ml more distillate were recovered from the trap.

[1]Mixture of $C_{10,12}$ alkoxylated alcohols containing 70% (wt.) ethylene oxide and marketed by Vista Chemical Company.

Case I

The procedure used in Control A was followed, with the exception that no aluminum trialkoxide was employed.

Case II

In this procedure, the procedure of Case I was followed, with the exception that the flask was fitted with a reflux condenser closed with a bellows to ensure that no water was lost during the reaction, i.e., during the catalyst preparation. No vacuum or nitrogen sparge was utilized.

Case III

In this procedure, the procedure as per Case II was followed, but all components were admixed at room temperature for 1 hour.

Case IV

The procedure used in Control A was employed, with the exception that there was no heating and hence no water removal, the ingredients being mixed together at ambient temperature for about 1 hour.

CONTROL B

In this procedure, Example 21 of U.S. Pat. No. 4,754,075 was followed to prepare the catalyst.

EXAMPLE 1

Various ethoxylated alcohols were made by reacting various alcohols with ethylene oxide to achieve ethoxylated alcohols containing a desired amount (weight percent) of ethylene oxide adduct. The results are shown in Tables 1, 2, and 3 below.

TABLE 1

Preparation of Ethoxylated $C_{10}$ Alcohol Containing 40% Ethylene Oxide

| Catalyst | Catalyst wt. (g) (per 300 g ETO) | EO Addition Time (minutes) |
|---|---|---|
| Case I | 0.2 | 33.3 |
| Case I | 0.3 | 23.8 |
| Case II | 0.3 | 32.6 |
| Case III | 0.3 | 28.4 |
| Case IV | 1.5 | 364.0 |
| Control A | 0.2 | 48.2 |
| Control A | 0.4 | 20.0 |
| Control B | 15.0 | 15.0 |

TABLE 2

Preparation of Ethoxylated $C_{12,14}$ Alcohol Containing 30% Ethylene Oxide

| Catalyst | Catalyst wt. (g) | EO Addition Time (minutes) |
|---|---|---|
| Case II | 0.3 | 32.6 |
| Case III | 0.3 | 21.6 |
| Control B | 15.0 | 25.3 |

TABLE 3

Preparation of Ethoxylated $C_{12,14}$ Alcohol Containing 70% Ethylene Oxide

| Catalyst | Catalyst wt. (g) | EO Addition Time (minutes) |
|---|---|---|
| Case I | 0.3 | 27.8 |
| Case III | 0.3 | 32.0* |
| Control B | 15.0 | 61.1 |

*Analytical Data:
Free alcohol level 0.08%
Polyethylene glycol 0.21%

As can be seen from the data in Tables 1, 2, and 3, catalysts made without removal of water or aluminum trialkoxide are active alkoxylation catalysts as compared with the catalysts disclosed in U.S. Pat. Nos. 4,754,075 and 4,835,321 (see Case I, Case II, and Case III of Tables 1, 2, and 3). Indeed, as can be seen from Case III in Table 2, a procedure that involves no addition of aluminum trialkoxide or heating, and hence no loss of water, produces the most active catalyst on a per unit weight basis. It should also be observed with respect to Case III in Table 3 that in the absence of any heating and hence no water removal, very high alcohol conversions and very low by-product polyethylene glycol levels are obtained during the ethoxylation procedure. Conversely, if the procedure of U.S. Pat. No. 4,835,321 is followed but without heating (see Case IV, Table 1), a largely ineffective catalyst is produced.

EXAMPLE 2

This example demonstrates the effect of the presence of the carboxylic acid in the catalyst. A series of $C_{12,14}$ alcohols were ethoxylated to produce ethoxylated alcohols containing 70% by weight ethylene oxide adduct using the catalysts prepared by the procedure of Case III. The results are shown in Table 4 below.

TABLE 4

| Entry | Catalyst | Calcium Used (moles) | Ca/Acid (mole ratio) | EO Addition Time (min.) |
|---|---|---|---|---|
| 1 | Ca(OH)$_2$, 2-EH[1] | 3.21 ± 10$^{-4}$ | 8.5:1 | 53.8 |
| 2 | Ca(OH)$_2$, 2-EH | 3.16 ± 10$^{-4}$ | 1:1 | 116 |
| 3 | Ca(OH)$_2$, Ca(2-EH)$_2$[2] | 2.59 ± 10$^{-4}$ | 1:1 | 66.3 |
| 4 | Ca(2-EH)$_2$ | 2.57 ± 10$^{-4}$ | 1:2 | 122.3 |

[1] 2-Ethyl hexanoic acid
[2] Calcium salt of 2-ethylhexanoic acid

As can be seen from the data in Table 4, presence of the carboxylic acid, particularly a branched carboxylic acid, greatly enhances catalytic activity. On the other hand, it can be observed that when too much carboxylic acid is present, catalytic activity is lower. For example, with respect to entries 1 and 2 in Table 4, at a calcium/acid ratio of 8.5:1, the catalyst is more than twice as active than when the calcium/acid ratio is 1:1. A like result is seen with respect to entries 3 and 4, when the calcium salt of 2-ethylhexanoic acid is used in place of the free acid.

The foregoing description and examples illustrate selected embodiments of the present invention. In light thereof, variations and modifications will be suggested to one skilled in the art, all of which are in the spirit and purview of this invention.

What is claimed is:

1. A process for preparing an alkoxylation catalyst comprising:

admixing an alkoxylated alcohol mixture, a calcium-containing compound that is at least partially dispersible in said alkoxylated alcohol mixture and a carboxylic acid having from about 4 to about 15 carbon atoms, the mole ratio of calcium to said carboxylic acid being from about 15:1 to 1:1, to produce a calcium-containing composition having titratable alkalinity, said calcium-containing composition being obtained under conditions to prevent loss of water; and adding an amount of an inorganic acid to neutralize at least 25% of said titratable alkalinity under conditions to prevent loss of water to produce a partially neutralized calcium-containing catalyst.

2. The process of claim 1 including heating said partially neutralized composition at a temperature of from about 90° to about 130° C. under reflux conditions.

3. The process of claim 2 wherein said heating is conducted for a period of 1 to 5 hours.

4. The process of claim 1 wherein said calcium-containing compound is selected from the group consisting of calcium oxide, calcium hydroxide, and mixtures thereof.

5. The process of claim 1 wherein said inorganic acid is selected from the group consisting of sulfuric acid, phosphoric acid, and hydrochloric acid.

6. An alkoxylation process comprising:

forming an alkoxylation catalyst by admixing an alkoxylated alcohol mixture, a calcium-containing compound that is at least partially dispersible in said alkoxylated alcohol mixture, and a carboxylic acid having from about 4 to about 15 carbon atoms, the mole ratio of calcium to said carboxylic acid being from about 15:1 to 1:1, to produce a calcium-containing composition having titratable alkalinity, said calcium-containing composition being obtained under conditions to prevent loss of water;

adding an amount of inorganic acid to neutralize at least 25% of said titratable alkalinity under conditions to prevent loss of water to produce a partially neutralized calcium-containing alkoxylation catalyst;

reacting, in the presence of said alkoxylation catalyst, a reactant selected from the group consisting of compounds having active hydrogen atoms, esters, and mixtures thereof and an alkylene oxide under alkoxylation conditions to produce an alkoxylated derivative of said reactant.

7. The process of claim 6 including heating said partially neutralized composition at a temperature of from about 90° C. to about 130° C. under reflux conditions.

8. The process of claim 7 wherein said heating is conducted for a period of 1 to 5 hours.

9. The process of claim 6 wherein said alkoxylation is conducted at a temperature of from about 80° C. to about 200° C.

10. The method of claim 6 wherein said reactant comprises an alcohol having the formula:

$$R_1-(OH)_x$$

wherein $R_1$ is a hydrocarbon radical containing from about 1 to about 30 carbon atoms and x is 1 to 10.

11. The process of claim 10 wherein R is a hydrocarbon radical containing from about 8 to about 14 carbon atoms.

12. The process of claim 6 wherein said alcohol reactant is a monohydric aliphatic alcohol containing from about 8 to about 14 carbon atoms.

13. The process of claim 6 wherein said calcium-containing compound is selected from the group consisting of calcium oxide, calcium hydroxide, and mixtures thereof.

14. The process of claim 6 wherein said inorganic acid is selected from the group consisting of sulfuric acid, phosphoric acid, and hydrochloric acid.

15. The process of claim 6 wherein said alkylene oxide comprises ethylene oxide.

16. The process of claim 6 wherein said reactant comprises an ester.

* * * * *